(12) United States Patent
Jung (10) Patent No.: US 9,661,318 B2
(45) Date of Patent: May 23, 2017

(54) METHOD AND APPARATUS FOR INSPECTING FLAT PANEL DISPLAY

(71) Applicant: Samsung Display Co., Ltd., Yongin, Gyeonggi-Do (KR)

(72) Inventor: Seung Hwan Jung, Seoul (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 1135 days.

(21) Appl. No.: 13/767,973

(22) Filed: Feb. 15, 2013

(65) Prior Publication Data
US 2014/0022376 A1 Jan. 23, 2014

(30) Foreign Application Priority Data
Jul. 20, 2012 (KR) .......................... 10-2012-0079490

(51) Int. Cl.
*H04N 9/47* (2006.01)
*H04N 7/18* (2006.01)
(Continued)

(52) U.S. Cl.
CPC ......... *H04N 17/00* (2013.01); *G01N 21/8851* (2013.01); *G01N 21/956* (2013.01);
(Continued)

(58) Field of Classification Search
CPC ...................................................... H04N 17/00
(Continued)

(56) References Cited

U.S. PATENT DOCUMENTS 5,898,800 A * 4/1999 Gahang .................... G06K 9/38
382/223
6,002,813 A * 12/1999 Cho ....................... G06T 3/4007
348/458

(Continued)

FOREIGN PATENT DOCUMENTS

KR WO 2006080760 A1 * 8/2006 ......... G01N 21/8803
KR 10-1094304 B1 12/2011

OTHER PUBLICATIONS

Watson, "Perimetric complexity of binary digital images", The Mathematica Journal, Journal 14 @ 2012 Wolfram Media, Inc. Published Feb. 17, 2012.*

(Continued)

*Primary Examiner* — Jamie Atala
*Assistant Examiner* — Richard A Hansell, Jr.
(74) *Attorney, Agent, or Firm* — Robert E. Bushnell, Esq.

(57) ABSTRACT

In a method and apparatus for optically inspecting an FPD in a reduced time, the apparatus for inspecting the flat panel display (FPD) comprises a lighting device separated from a top surface of an object and emitting light toward the top surface of the object, a photographing device separated from the top surface of the object and photographing an image using light emitted from the lighting device and then reflected by the top surface of the object, a controller controlling the lighting device and the photographing device to move in a plane separated from and parallel to the top surface of the object, and an image processor connected to the photographing device and processing the photographed image, wherein the image processor samples some of pixels included in the photographed image and converts the sampled pixels to binary form.

11 Claims, 3 Drawing Sheets

(51) Int. Cl.
  *H04N 17/00* (2006.01)
  *G01N 21/88* (2006.01)
  *G01N 21/956* (2006.01)

(52) U.S. Cl.
  CPC .............. *G01N 2021/8887* (2013.01); *G01N 2021/95676* (2013.01)

(58) Field of Classification Search
  USPC .......................................................... 348/92
  See application file for complete search history.

(56) References Cited

U.S. PATENT DOCUMENTS

| | | | | |
|---|---|---|---|---|
| 6,415,063 | B1* | 7/2002 | Pourjavid | H04N 5/367 348/E5.081 |
| 6,898,329 | B1* | 5/2005 | Takahashi | G06K 9/38 358/3.2 |
| 6,950,210 | B2* | 9/2005 | Guo | G06K 9/38 358/1.9 |
| 7,623,216 | B2 | 11/2009 | Hwang | |
| 7,689,029 | B2 | 3/2010 | Onishi et al. | |
| 8,013,876 | B2 | 9/2011 | Chung et al. | |
| 8,145,008 | B2* | 3/2012 | Chen | G06T 7/0004 382/149 |
| 8,164,604 | B2 | 4/2012 | Chung et al. | |
| 2002/0088952 | A1* | 7/2002 | Rao | G01N 21/9501 250/559.45 |
| 2004/0213449 | A1 | 10/2004 | Safaee-Rad et al. | |
| 2005/0105152 | A1* | 5/2005 | Kang | G02B 5/32 359/22 |
| 2006/0017676 | A1* | 1/2006 | Bowers | G01N 21/278 345/87 |
| 2006/0164703 | A1* | 7/2006 | Coppola | G03H 1/0841 359/15 |
| 2008/0001869 | A1 | 1/2008 | Chung et al. | |
| 2008/0063254 | A1 | 3/2008 | Tanizaki et al. | |
| 2008/0170195 | A1 | 7/2008 | Kwon et al. | |
| 2011/0274342 | A1* | 11/2011 | Maeda | G01N 21/95623 382/149 |
| 2012/0038780 | A1* | 2/2012 | Jeon | G01N 21/95 348/189 |
| 2012/0086800 | A1* | 4/2012 | Vladimirsky | B82Y 10/00 348/128 |
| 2014/0160533 | A1* | 6/2014 | Fukamachi | H04N 1/405 358/3.06 |

OTHER PUBLICATIONS

Gimp threshold tool (Sect. 5.5) accessed via the web at http://docs.gimp.org/en/gimp-tool-threshold.html. Wayback machine used to show online availability of tool as of Jun. 18, 2006. See web archive link: http://web.archive.org/web/20061010192114/http://docs.gimp.org/en/gimp-tool-threshold.html (hard copy not provided due to PDF conversion issues).*

* cited by examiner

METHOD AND APPARATUS FOR INSPECTING FLAT PANEL DISPLAY

CLAIM OF PRIORITY

This application makes reference to, incorporates the same herein, and claims all benefits accruing under 35 U.S.C. §119 from an application earlier filed in the Korean Intellectual Property Office on the 20 of Jul. 2012 and there duly assigned Serial No. 10-2012-0079490.

BACKGROUND OF THE INVENTION

Field of the Invention

The present invention relates to a method and apparatus for inspecting a flat panel display (FPD), and more particularly, to a method and apparatus for optically inspecting an FPD in a reduced time.

Description of the Related Art

The development of information and communications technology and the diverse needs of the information society are increasing the demand for displays. Cathode ray tubes (CRTs), which were once the most common type of display devices, are being replaced with flat panel displays (FPDs) to meet the demand for more compact and less power-consuming display devices. Some of the most widely used FPDs include electroluminescent displays (ELDs), liquid crystal displays (LCDs) (TFT-LCDs, TN/STN), plasma display panels, and organic electroluminescent displays.

To maintain stable quality of an FPD, it is important to develop materials and processes. However, it is also important to remove defects in a panel (such as glass or plastic) used for the fabrication of the FPD.

In a conventional method of inspecting an FPD to find any defects, light is irradiated onto the panel surface, and defects in the panel surface are detected based on optical changes of the irradiated light. That is, light emitted from a light source reaches the FPD (i.e., a subject) after passing sequentially through a mirror, a lens, a liquid crystal plate, etc. Then, an inspector may determine the presence or absence of defects such as scratches or stains. However, if the luminance of the light is not stable, it may be impossible to accurately determine the presence or absence of defects due to the non-uniform brightness of the FPD.

Also, a method of automatically inspecting an FPD using a camera may be used to find any defects. However, if an image of the FPD is photographed and analyzed by the camera, a lot of time may be required to inspect the FPD.

SUMMARY OF THE INVENTION

The present invention provides a method and apparatus for inspecting a flat panel display (FPD) in a reduced time.

The present invention also provides a method and apparatus for inspecting a FPD in a reduced time with results similar to those of a conventional inspection method and apparatus when the proportion of stains in a total area of the FPD is small.

However, aspects of the present invention are not restricted to the ones set forth herein. The above and other aspects of the present invention will become more apparent to one of ordinary skill in the art to which the present invention pertains by referencing the detailed description of the present invention given below.

According to an aspect of the present invention, there may be provided an apparatus for inspecting a flat panel display (FPD), the apparatus comprising constructed with a lighting device being separated from a top surface of an object and emitting light toward the top surface of the object, a photographing device separated from the top surface of the object and photographing an image using light emitted from the lighting device and then reflected by the top surface of the object, a controller controlling the lighting device and the photographing device to move on a plane separated from and parallel to the top surface of the object, and an image processor connected to the photographing device and processing the photographed image, wherein the image processor samples some of pixels included in the photographed image and converts the sampled pixels to binary form The photographed image may be a 2D image, and the image processor samples some of the pixels included in the photographed image at a predetermined sampling interval in an X-axis direction and at a predetermined sampling interval in a Y-axis direction.

The sampling interval in the X-axis direction may be the same as the sampling interval in the Y-axis direction.

After converting a sampled pixel at coordinates (a, b) to binary form, the image processor may convert a pixel at coordinates (a+(the sampling interval in the X-axis direction), b) to binary form if the coordinates (a+(the sampling interval in the X-axis direction), b) are not outside the photographed image, converts a pixel at coordinates (0, b+(the sampling interval in the Y-axis direction)) to binary form if the coordinates (a+(the sampling interval in the X-axis direction), b) are outside the photographed image but if the coordinates (0, b+(the sampling interval in the Y-axis direction)) are not outside the photographed image, and terminates the processing of the photographed image if the coordinates (a+(the sampling interval in the X-axis direction), b) and the coordinates (0, b+(the sampling interval in the Y-axis direction)) are outside the photographed image.

After a pixel is converted to binary form, the pixel may be represented by one if a brightness value of the pixel is greater than a first threshold value and smaller than or equal to a second threshold value, and is represented by zero if the brightness value of the pixel is smaller than or equal to the first threshold value or greater than the second threshold value, and if a value obtained as a result of converting the sampled pixel at the coordinates (a, b) to binary form is one, the image processor converts to binary form all pixels existing in a (the sampling interval in the X-axis direction)× (the sampling interval in the Y-axis direction) range from the coordinates (a, b) in the photographed image.

After a pixel is converted to binary form, the pixel may be represented by one if a brightness value of the pixel is greater than the first threshold value and smaller than or equal to the second threshold and is represented by zero if the brightness value of the pixel is smaller than or equal to the first threshold value or greater than the second threshold value, and if the value obtained as a result of converting the sampled pixel to binary form at the coordinates (a, b) is one, the image processor converts to binary form all pixels existing in a square area having coordinates (a−(the sampling interval in the X-axis direction)/2, b−(the sampling interval in the Y-axis direction/2), coordinates (a+(the sampling interval in the X-axis direction)/2, b−(the sampling interval in the Y-axis direction/2), coordinates (a−(the sampling interval in the X-axis direction)/2, b+(the sampling interval in the Y-axis direction/2) and coordinates (a+(the sampling interval in the X-axis direction)/2, b+(the sampling interval in the Y-axis direction/2) as vertices in the photographed image.

A pixel may be represented by zero or one after being converted to binary form using a brightness value of the pixel.

A pixel may be represented by one if a brightness value of the pixel is greater than the first threshold value and smaller than or equal to the second threshold value and is represented by zero if the brightness value of the pixel is smaller than or equal to the first threshold value or greater than the second threshold value.

The image processor may sample some of the pixels included in the photographed image at a predetermined sampling interval.

The photographed image may be a black-and-white image or a color image.

According to an aspect of the present invention, there may be provided a method of inspecting a FPD, the method may be practiced by emitting light toward a top surface of an object, photographing an image using light reflected by the top surface of the object, sampling some of pixels included in the photographed image, and converting the sampled pixels to binary form.

The photographed image may be a 2D image, and the sampling of some of the pixels may be practiced by sampling some of the pixels included in the photographed image at a predetermined sampling interval in an X-axis direction and at a predetermined sampling interval in a Y-axis direction.

The sampling interval in the X-axis direction may be the same as the sampling interval in the Y-axis.

The converting to binary form of the sampled pixels may be practiced by obtaining coordinates of a next sample pixel in the photographed image using the sampling interval in the X-axis direction and the sampling interval in the Y-axis direction and moving from current coordinates to the coordinates of the next sample pixel, converting to binary form a the sample pixel at the current coordinates, and determining whether the sample pixel at the current coordinates is a last sample pixel, repeating operations extending from the moving from the current coordinates to the coordinates of the next sample pixel to conversion of the sample pixel to binary form at the current coordinates if the sample pixel at the current coordinates is not the last sample pixel.

In moving from the current coordinates to the coordinates of the next sample pixel, when the current coordinates are coordinates (a, b), the coordinates of the next sample pixel may be coordinates (a+(the sampling interval in the X-axis direction), b) if the coordinates (a+(the sampling interval in the X-axis direction), b) are not outside the photographed image, and the coordinates of the next sample pixel are coordinates (0, b+(the sampling interval in the Y-axis direction)) if the coordinates (a+(the sampling interval in the X-axis direction), b) are outside the photographed image but if the coordinates (0, b+(the sampling interval in the Y-axis direction)) are not outside the photographed image.

After a pixel is converted to binary form, the pixel may be represented by one if a brightness value of the pixel is greater than a first threshold value and smaller than or equal to a second threshold and is represented by zero if the brightness value of the pixel is smaller than or equal to the first threshold value or greater than the second threshold value, and, if a value obtained as a result of binarizing the sample pixel at the current coordinates is one, converting to binary form all pixels existing in a (the sampling interval in the X-axis direction)×(the sampling interval in the Y-axis direction) range from the current coordinates in the photographed image between the converting to binary form of the sample pixel at the current coordinates and the repeating of the operations, and when repeating these operations, those operations ranging from the movement from the current coordinates to the coordinates of the next sample pixel to the conversion to binary form of the sample pixel at the current coordinates are repeated if the sample pixel at the current coordinates is not the last sample pixel.

After a pixel is converted to binary form, the pixel may be represented by one if a brightness value of the pixel is greater than the first threshold value and smaller than or equal to the second threshold and is represented by zero if the brightness value of the pixel is smaller than or equal to the first threshold value or greater than the second threshold value, further comprising, if the value obtained as a result of converting to binary form the sample pixel at the coordinates is one, when the current coordinates are coordinates (a, b), converting to binary form all pixels existing in a square area having coordinates (a−(the sampling interval in the X-axis direction)/2, b−(the sampling interval in the Y-axis direction)/2), coordinates (a+(the sampling interval in the X-axis direction)/2, b−(the sampling interval in the Y-axis direction)/2), coordinates (a−(the sampling interval in the X-axis direction)/2, b+(the sampling interval in the Y-axis direction)/2) and coordinates (a+(the sampling interval in the X-axis direction)/2, b+(the sampling interval in the Y-axis direction)/2) as vertices in the photographed image, and in the repeating of the operations, the operations extending from the movement from the current coordinates to the coordinates of the next sample pixel to the conversion to binary form of the sample pixel at the current coordinates are repeated if the sample pixel at the current coordinates is not the last sample pixel.

A pixel may be represented by zero or one after being converted to binary form using a brightness value of the pixel.

A pixel may be represented by one if a brightness value of the pixel is greater than the first threshold value and smaller than or equal to the second threshold value and is represented by zero if the brightness value of the pixel is smaller than or equal to the first threshold value or greater than the second threshold value.

The sampling of some of the pixels may comprise sampling some of the pixels included in the photographed image at a predetermined sampling interval.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein.

DETAILED DESCRIPTION OF THE INVENTION

Advantages and features of the present invention and methods of accomplishing the same may be understood more readily by reference to the following detailed description of preferred embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Thus, in some embodiments, well-known structures and devices are not shown in order not to obscure the description of the invention with unnecessary detail. Like numbers refer to like elements throughout. In the drawings, the thickness of layers and regions are exaggerated for clarity.

It will be understood that, when an element or layer is referred to as being "on," or "connected to" another element or layer, it can be directly on or connected to the other element or layer or intervening elements or layers may be present. In contrast, when an element is referred to as being "directly on" or "directly connected to" another element or layer, there are no intervening elements or layers present. As used herein, the term "and/or" includes any and all combinations of one or more of the associated listed items.

Spatially relative terms, such as "below," "beneath," "lower," "above," "upper," and the like, may be used herein for ease of description to describe the relationship of one element or feature to another element(s) or feature(s) as illustrated in the figures. It will be understood that the spatially relative terms are intended to encompass different orientations of the device in use or operation in addition to the orientation depicted in the figures.

Embodiments described herein will be described by referring to planar views and/or cross-sectional views by way of ideal schematic views of the invention. Accordingly, the exemplary views may be modified depending on manufacturing technologies and/or tolerances. Therefore, the embodiments of the invention are not limited to those shown in the views, but include modifications in configuration formed on the basis of manufacturing processes. Therefore, regions exemplified in figures have schematic properties and shapes of regions shown in figures, exemplify specific shapes of regions of elements, and do not limit aspects of the invention.

A method and apparatus for inspecting a flat panel display (FPD) according to an embodiment of the present invention will now be described in more detail with reference to the attached drawings.

Figure 1:
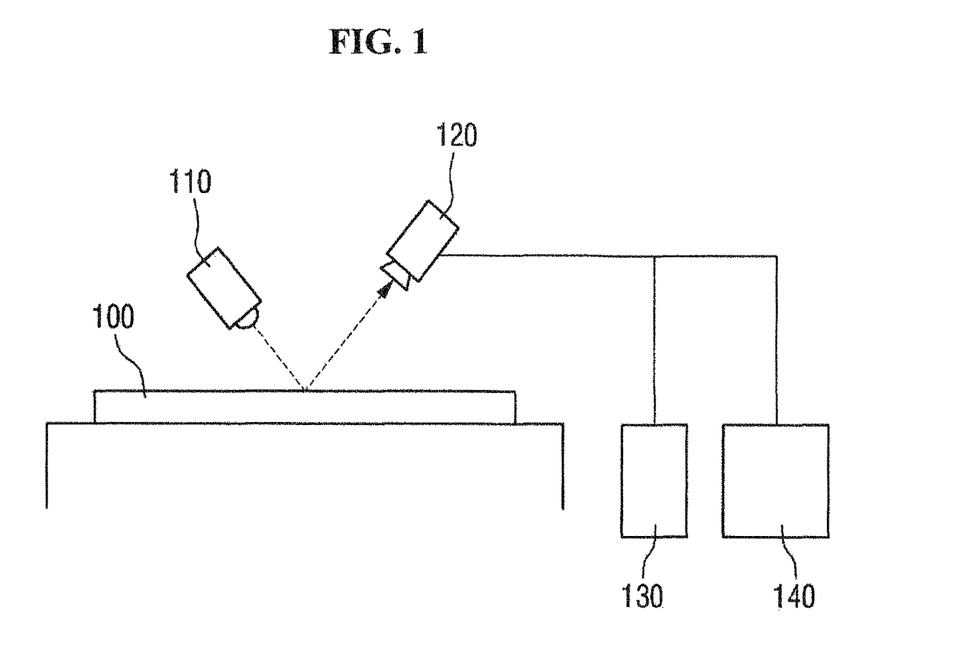
FIG. 1 is a perspective view of an apparatus for inspecting a flat panel display (FPD) according to an embodiment of the present invention.

FIG. 1 is a perspective view of an apparatus for inspecting an FPD according to an embodiment of the present invention. Referring to FIG. 1, the FPD inspection apparatus according to the current embodiment may include a lighting device 110, a photographing device 120, a controller 130, and an image processor 140. The lighting device 110 is separated from a top surface of an object 100 and emits light toward the top surface of the object 100. The photographing device 120 is separated from the top surface of the object 100 and photographs light emitted from the lighting device 110 and then reflected by the top surface of the object 100. The controller 130 controls the lighting device 110 and the photographing device 120 to move on a plane separated from and parallel to the top surface of the object 100. The image processor 140 is connected to the photographing device 120 and processes an image photographed by the photographing device 120.

Specifically, the lighting device 110 may be separated from the top surface of the object 100. The object 100 may be any object that can be optically inspected by the FPD inspection apparatus. The object 100 may be, e.g., an organic light-emitting diode (OLED) panel. The lighting device 110 may emit light toward the top surface of the object 100.

The photographing device 120 may be separated from the top surface of the object 100. The photographing device 120 may photograph light emitted from the lighting device 110 and then reflected by the top surface of the object 100. The photographing device 120 may be, e.g., a camera.

The controller 130 may control movement of the lighting device 110 and the photographing device 120. The controller 130 may move the photographing device 120 so that the photographing device 120 can photograph each portion of the top surface of the object 100. In addition, since the photographing device 120 photographs light emitted from the lighting device 110, the controller 130 may move the lighting device 110 together with the photographing device 120. The controller 130 may control the photographing device 120 to move in a plane separated from and parallel to the top surface of the object 100, so that the photographing device 120 can uniformly photograph light reflected by the top surface of the object 100. In addition, the controller 130 may control the lighting device 110 to move in the plane.

The image processor 140 may be connected to the photographing device 120. The image processor 140 may receive an image photographed by the photographing device 120 and may process the received image. Depending on the type of the photographing device 120, the image photographed by the photographing device 120 may be a black-and-white image or a color image.

The image processor 140 may process the image in various ways according to the inspection purpose. Generally, the purpose of inspecting an FPD is to identify whether the composition of the FPD is uniform, find a defect in the FPD, and detect the position of the defect. The following description will be based on an embodiment in which the position of a stain is detected using light emitted to, and then reflected by, an FPD. That is, the object 100 may be an FPD.

The image processor 140 may convert an image photographed by the photographing device 120 to binary form to determine whether light reflected from a point on the top surface of the object 100 corresponds to a normal portion or a stain.

Conversion to binary form is a process of obtaining a binary image (0 or 1) by processing a black-and-white image, the pixels of which may have different brightnesses, or a color image whose pixels may have different colors. To convert an image to binary form, a value of each pixel of the image may be compared with a threshold value. Conversion to binary form can be used to detect a certain area in the entire image, and various geometric analyses can be carried out using an image converted to binary form.

Figure 2:
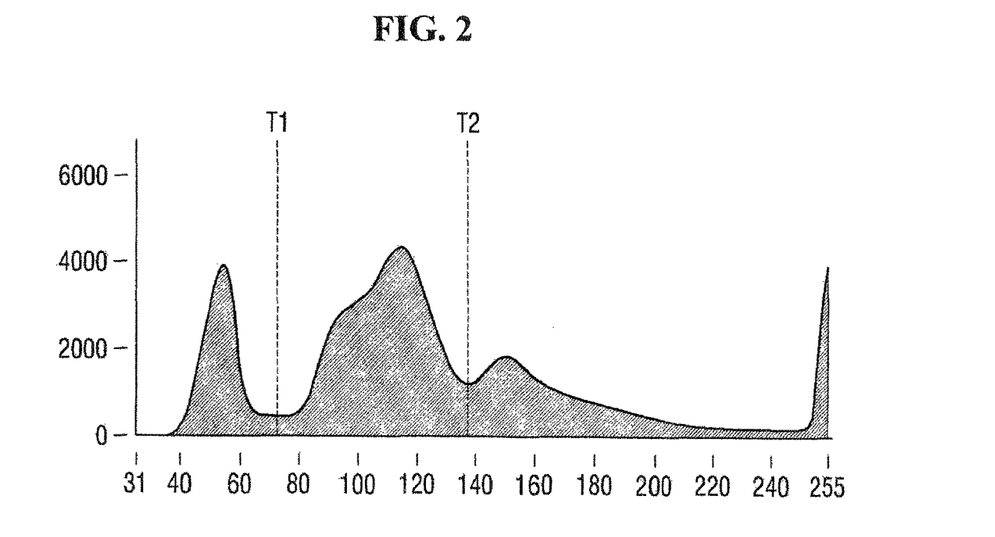
FIG. 2 is a color histogram illustrating a method of converting to binary form according to an embodiment of the present invention.

FIG. 2 is a color histogram illustrating a method of converting to binary form according to an embodiment of the present invention. Referring to FIG. 2, the horizontal axis of the color histogram is brightness represented by 256 gray levels, and the vertical axis is the number of pixels that have each brightness value. The color histogram of FIG. 2 may be obtained as a result of photographing and analyzing light reflected from all portions of a top surface of an object of the same type as the object 100.

Referring to the histogram of FIG. 2, the number of pixels is large in an area with a brightness value of 40 to 60 and in an area with a brightness value of 80 to 130. That is, it can be understood that an original image having a color histogram as shown FIG. 2 consists mainly of a dark area with a brightness value of 40 to 60 and a bright area with a brightness value of 80 to 130. Therefore, a group of pixels having brightness values smaller than or equal to T1 may be determined to be the dark area, and a group of pixels having brightness values greater than T2 may be determined to be noise. Therefore, a group of pixels having brightness values greater than T1 and smaller than or equal to T2 may be determined to be the bright area.

The above original image was obtained by photographing the light reflected from all portions of the top surface of the object which has the same type as the object 100. Therefore, the original image may be a 2D image. It may be assumed that coordinates of a pixel in the image is (x, y) and that a brightness value of the pixel at the coordinates (x, y) is f(x, y).

In the current embodiment, after each pixel of an image is converted to binary form, pixels (bright area) with brightness values greater than T1 and smaller than or equal to T2 may have a value of one as a result of the conversion to binary form while pixels with brightness values smaller than or equal to T1, or pixels with brightness values greater than T2 have a value of zero as a result of the conversion to binary form. Therefore, each pixel may be converted to binary form using the following function. The result of conversion to binary form a pixel at (x, y) may be represented by g(x, y).

$$g(x, y) = \begin{cases} 1 & (T1 < f(x, y) <= T2) \\ 0 & (\text{otherwise}) \end{cases} \quad (1)$$

If the time required to convert a pixel to binary form is Tp, the time T required to convert to binary form all pixels of a 2D image having (W pixels)×(H pixels) may be given by Equation (2).

$$T=Tp*W*H \quad (2)$$

Therefore, if all pixels of an image photographed using light reflected from all portions of the top surface of the object 100 are converted to binary form, the time required to convert the pixels of the photographed image to binary form is proportional to the size of the top surface of the object 100 or the size of the photographed image. Therefore, if the photographed image has high resolution, a lot of time is required for conversion to binary form. Accordingly, a lot of time may be required to process the image using the results of conversion to binary form.

A method of inspecting an FPD according to an embodiment of the present invention can reduce the time required to inspect an FPD by solving the above problem. Furthermore, when the proportion of stains in the total area of the FPD is small, the inspection method according to the embodiment of the present invention can obtain results similar to those of a conventional inspection method while reducing the inspection time.

Figure 3:
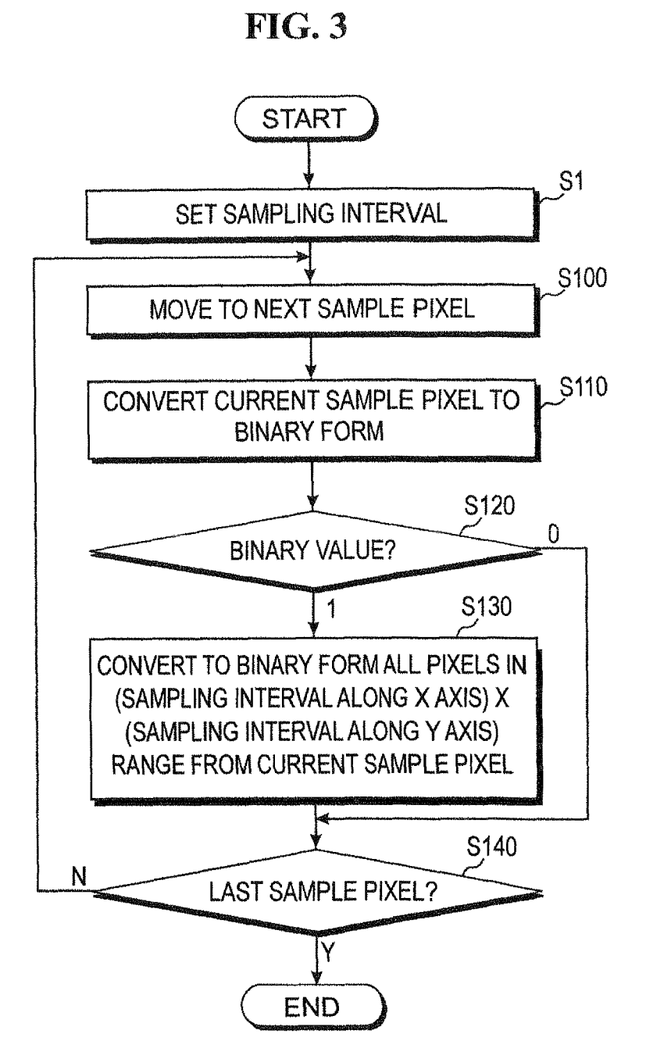
FIG. 3 is a flowchart illustrating a process of inspecting an FPD according to an embodiment of the present invention.

FIG. 3 is a flowchart illustrating a process of inspecting an FPD according to an embodiment of the present invention.

Figure 4:
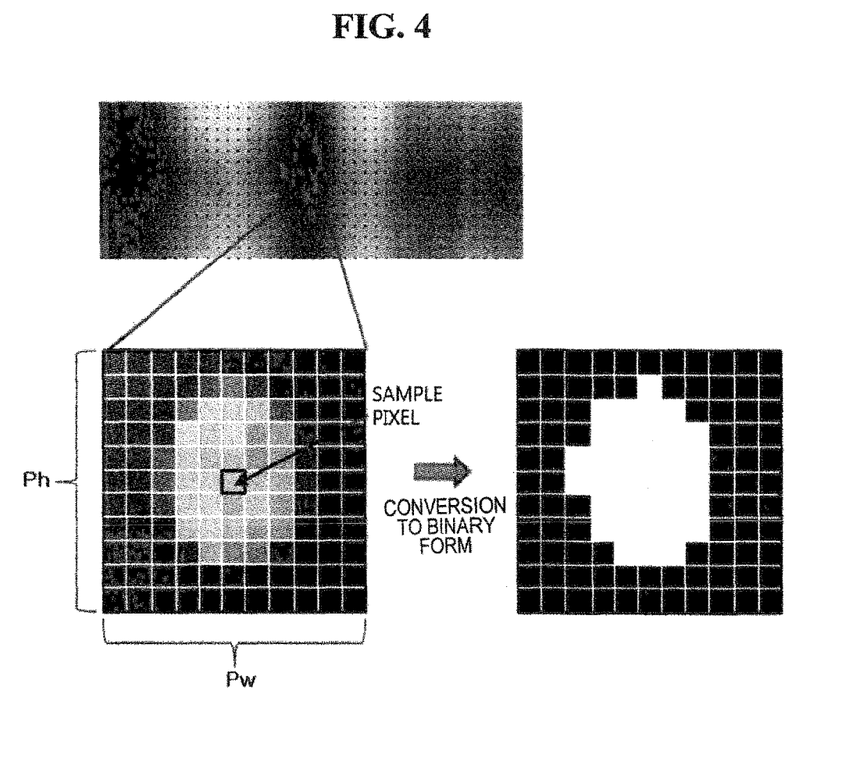
FIG. 4 is a reference diagram illustrating a method of inspecting an FPD according to an embodiment of the present invention.

FIG. 4 is a reference diagram illustrating a method of inspecting an FPD according to an embodiment of the present invention.

Referring to FIG. 3, in the FPD inspection method according to the current embodiment, an interval between pixels to be sampled from the entire image may be set (operation S1). The interval between the pixels to be sampled may be determined using various methods according to the inspection purpose. The interval may be determined to be ⅛ of an expected size of a bright area which corresponds to, e.g., stains. The interval between the pixels to be sampled may be set to the determined interval, and, accordingly, the pixels may be sampled at the set intervals. In the case of a 2D image, a sampling interval in an X-axis direction and a sampling interval in a Y-axis direction may be set independently or may be set to the same value. An embodiment in which the sampling interval in the X-axis direction is the same as the sampling interval in the Y-axis direction will hereinafter be described, and the sampling interval may be indicated by i.

Next, the position of a next sample pixel in the image is obtained based on the set interval, and a current position is moved to the position of the next sample pixel (operation S100). Sampling may start from coordinates (0, 0). It may be assumed that coordinates of a current sample pixel are (a, b) and that coordinates of a next sample pixel are (c, d). Values of c and d may be obtained using various methods depending on the embodiment. In the current embodiment, pixels may be sampled sequentially at the sampling intervals. Therefore, the coordinates of the next sample pixel may be (a+i, b) or (a, b+i). In an embodiment to be described hereinafter, a process of sampling pixels along the X axis of an image and then along the X axis again after moving along the Y axis by i is repeated.

Therefore, if a pixel at (a, b) is sampled, candidate coordinates of a next sample pixel may be (a+i, b). If a position corresponding to (a+i, b) is outside the image, the candidate coordinates of the next sample pixel may be (0, b+i). If a position corresponding to (0, b+i) is outside the image, it may be determined that there are no more sample pixels, and the sampling operation is terminated.

Next, a pixel at the current position is converted to binary form (operation S110). Here, the conversion method described above may be used.

Next, it is determined whether a value obtained as a result of converting the pixel to binary form is one or zero (operation S120). If the obtained value is one, all pixels existing in a (sampling interval along the X axis)×(sampling interval along the Y axis) range from the current position in the image may be converted to binary form (operation S130). In the current embodiment, the sampling interval along the X axis and the sampling interval along the Y axis are all i. Therefore, when the current position is (a, b), all pixels existing within a square area having (a−i/2, b−i/2), (a+i/2, b−i/2), (a−i/2, b+i/2), and (a+i/2, b+i/2) as its vertices may be converted to binary form.

Referring to the embodiment of FIG. 4, a sample pixel in a bright area is sampled. If the sample pixel is converted to binary form, 1 may be obtained as a result. In the embodiment of FIG. 4, a sampling interval Pw along the X axis and a sampling interval Ph along the Y axis are all 11. Therefore, all pixels existing in an 11×11 range from the sample pixel may be converted to binary form, and the results are shown in the lower right portion of FIG. 4.

If the value obtained as a result of converting the pixel to binary form at the current position is zero, a next operation may be performed by skipping operation S130.

Next, it is determined whether the pixel at the current position is a last sample pixel (operation S140 of FIG. 3). If the pixel at the current position is not the last sample pixel, operations S100 through S130 may be repeated. If the pixel at the current position is the last sample pixel, the FPD inspection process may be terminated. Whether the pixel at the current position is the last sample pixel may be determined using a method similar to the method used in operation S100.

In the FPD inspection method according to the current embodiment of the present invention, the time T' required to convert to binary form a 2D image having (W pixels)×(H pixels) can be calculated using the following equation. In the following equation, Pw indicates the sampling interval along the X axis, and Ph indicates the sampling interval along the Y axis. In addition, C indicates the number of pixels having one as a g(x, y) value from among all sampled pixels.

$$T' = Tp * \frac{W}{Pw} * \frac{H}{Ph} + Tp * C * (Pw * Ph - 1) \quad (3)$$

Here, since C indicates the number of pixels having one as the g(x, y) value from among all sampled pixels, the following inequality can be established.

$$C <= \frac{W}{Pw} * \frac{H}{Ph} \quad (4)$$

Therefore, the time T' required in the FPD inspection method according to the current embodiment is smaller than or equal to the time T required to binarize all pixels in the conventional inspection method.

In this regard, the FPD inspection method according to the current embodiment can reduce the inspection time. In particular, when the proportion of stains in the size of the entire image is small, C is reduced further, resulting in a further reduction of the inspection time.

Figure 5:
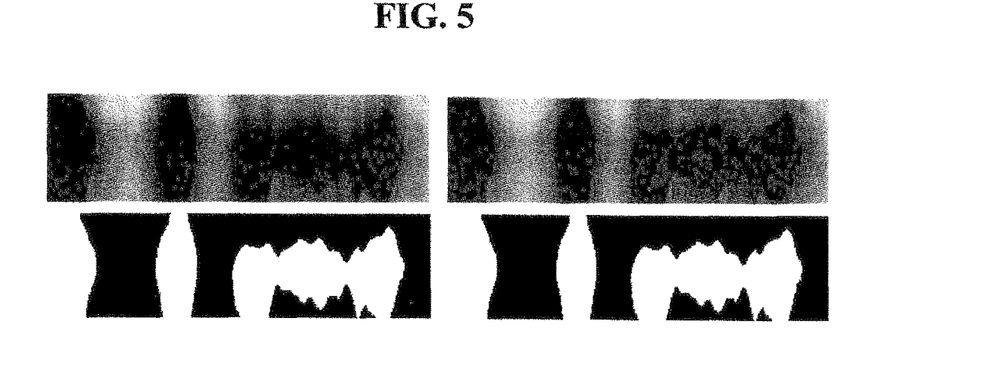
FIG. 5 is a reference diagram for comparing a result of conversion to binary form according to a conventional method with a result of conversion to binary form according to an embodiment of the present invention.

FIG. 5 is a reference diagram for comparing a result of conversion to binary form according to a conventional method with a result of conversion to binary form according to an embodiment of the present invention. On the left side of FIG. 5 is shown a result of converting all pixels of a photographed image to binary form using the conventional method. On the right side of FIG. 5 is shown a result of converting the photographed image to binary form using the FPD inspection method according to the embodiment of the present invention.

As apparent from the conversion results shown in FIG. 5, when conversion to binary form is performed using the FPD inspection method according to the embodiment of the present invention, similar results can be obtained while the inspection time is reduced, as compared with when conversion to binary form is performed using the conventional inspection method.

According to an embodiment of the present invention, an FPD can be inspected in a reduced time.

According to an embodiment of the present invention, when the proportion of stains in a total area of the FPD is small, the FPD can be inspected in a reduced time with similar results to a conventional inspection method.

While the present invention has been particularly shown and described with reference to exemplary embodiments thereof, it will be understood by those of ordinary skill in the art that various changes in form and detail may be made therein without departing from the spirit and scope of the present invention as defined by the following claims. It is therefore desired that the present embodiments be considered in all respects as illustrative and not restrictive, reference being made to the appended claims rather than the foregoing description to indicate the scope of the invention.

What is claimed is:

1. An apparatus inspecting a flat panel display (FPD), the apparatus comprising:
    a lighting device separated from a top surface of an object and emitting light toward the top surface of the object;
    a photographing device separated from the top surface of the object and photographing an image using light emitted from the lighting device and then reflected by the top surface of the object;
    a controller controlling the lighting device and the photographing device to move in a plane separated from and parallel to the top surface of the object; and
    an image processor connected to the photographing device processing the photographed image,
    wherein the image processor:
        samples, in the photographed image, some of single pixels of which each is surrounded by independent and non-selected pixels which are not sampled, and converts the sampled pixels to binary form,
        wherein the photographed image is a 2D image, and the sampled pixels are included in the photographed image at a predetermined sampling interval in an X-axis direction and at a predetermined sampling interval in a Y-axis direction,
        wherein after the sampled pixel is converted to binary form, the sampled pixel is represented by one if a brightness value of the pixel is greater than a first threshold value and smaller than or equal to a second threshold, and the sampled pixel is represented by zero if the brightness value of the pixel is smaller than or equal to the first threshold value or greater than the second threshold value, and if a value obtained as a result of converting to binary form the sampled pixel at the coordinates (a, b) is one, the image processor converts to binary form all pixels existing in a (the sampling interval in the X-axis direction)×(the sampling interval in the Y-axis direction) range from the coordinates (a, b) in the photographed image.

2. The apparatus of claim 1, wherein the sampling interval in the X-axis direction is the same as the sampling interval in the Y-axis.

3. The apparatus of claim 1, wherein after converting to binary form a sampled pixel at coordinates (a, b), the image processor
    converts to binary form a pixel at coordinates (a+(the sampling interval in the X-axis direction), b) if the coordinates (a+(the sampling interval in the X-axis direction), b) are not outside the photographed image,
    converts to binary form a pixel at coordinates (0, b+(the sampling interval in the Y-axis direction)) if the coordinates (a+(the sampling interval in the X-axis direction), b) are outside the photographed image but if the coordinates (0, b+(the sampling interval in the Y-axis direction)) are not outside the photographed image, and
    terminates the processing of the photographed image if the coordinates (a+(the sampling interval in the X-axis direction), b) and the coordinates (0, b+(the sampling interval in the Y-axis direction)) are outside the photographed image.

4. The apparatus of claim 1, wherein,
when the value obtained as a result of converting to binary form the sampled pixel at the coordinates (a, b) is one, the image processor converts to binary form all the non-selected pixels existing in a square area having:
coordinates (a−(the sampling interval in the X-axis direction)/2, b−(the sampling interval in the Y-axis direction/2),
coordinates (a+(the sampling interval in the X-axis direction)/2, b−(the sampling interval in the Y-axis direction/2),
coordinates (a−(the sampling interval in the X-axis direction)/2, b+(the sampling interval in the Y-axis direction/2) and
coordinates (a+(the sampling interval in the X-axis direction)/2, b+(the sampling interval in the Y-axis direction/2) as vertices in the photographed image.

5. The apparatus of claim 1, wherein a sampled pixel is represented by one of zero and one after being converted to binary form using a brightness value of the sampled pixel.

6. The apparatus of claim 1, wherein the photographed image is one of a black-and-white image and a color image.

7. A method of inspecting an FPD, the method comprising the steps of:
emitting light toward a top surface of an object;
photographing an image using light reflected by the top surface of the object;
sampling, in the photographed image, some of single pixels of which each is surrounded by independent and non-selected pixels which are not sampled; and
converting the sampled pixels to binary form,
wherein the photographed image is a 2D image, and the sampling of some of the single pixels comprises sampling some of the pixels included in the photographed image at a predetermined sampling interval in an X-axis direction and at a predetermined sampling interval in a Y-axis direction,
wherein the step of converting the sampled pixels to binary form comprises:
obtaining coordinates of a next sample pixel in the photographed image using the sampling interval in the X-axis direction and the sampling interval in the Y-axis direction and moving from current coordinates to coordinates of a next sample pixel;
converting to binary form a sample pixel at the current coordinates; and
determining whether the sample pixel at the current coordinates is a last sample pixel, repeating operations ranging from the moving from the current coordinates to the coordinates of the next sample pixel to the converting to binary form the sample pixel at the current coordinates when the sample pixel at the current coordinates is not the last sample pixel,
wherein after a pixel is converted to binary form, the pixel is represented by one when a brightness value of the pixel is greater than a first threshold value and is not greater than a second threshold, and is represented by zero when the brightness value of the pixel is not greater than the first threshold value or is greater than the second threshold value, further comprising, when a value obtained as a result of converting to binary form the sample pixel at the current coordinates is one, converting to binary form all pixels existing in a (the sampling interval in the X-axis direction)×(the sampling interval in the Y-axis direction) range from the current coordinates in the photographed image between the converting to binary form of the sample pixel at the current coordinates and the repeating of the operations, and in the repeating of the operations, the operations ranging from the moving from the current coordinates to the coordinates of the next sample pixel to the converting to binary form of the sample pixel at the current coordinates are repeated when the sample pixel at the current coordinates is not the last sample pixel.

8. The method of claim 7, wherein the sampling interval in the X-axis direction is the same as the sampling interval in the Y-axis.

9. The method of claim 7, wherein in the moving from the current coordinates to the coordinates of the next sample pixel, when the current coordinates are coordinates (a, b),
the coordinates of the next sample pixel are coordinates (a+(the sampling interval in the X-axis direction), b) when the coordinates (a+(the sampling interval in the X-axis direction), b) are not of outside the photographed image, and
the coordinates of the next sample pixel are coordinates (0, b+(the sampling interval in the Y-axis direction)) when the coordinates (a+(the sampling interval in the X-axis direction), b) are outside the photographed image but when the coordinates (0, b+(the sampling interval in the Y-axis direction)) are not outside of the photographed image.

10. The method of claim 7, wherein after the sampled pixel is converted to binary form,
the sampled pixel is represented by one when a brightness value of the sampled pixel is greater than the first threshold value and is not greater than the second threshold, and is represented by zero when the brightness value of the sampled pixel is not greater than the first threshold value or is greater than the second threshold value, further comprising,
when the value obtained as a result of converting to binary form the sampled pixel is one, when the current coordinates are coordinates (a, b), converting to binary form all the non-selected pixels existing in a square area having
coordinates (a−(the sampling interval in the X-axis direction)/2, b−(the sampling interval in the Y-axis direction)/2),
coordinates (a+(the sampling interval in the X-axis direction)/2, b−(the sampling interval in the Y-axis direction)/2),
coordinates (a−(the sampling interval in the X-axis direction)/2, b+(the sampling interval in the Y-axis direction)/2) and
coordinates (a+(the sampling interval in the X-axis direction)/2, b+(the sampling interval in the Y-axis direction)/2) as vertices in the photographed image, and
in the repeating of the operations, the operations ranging from the moving from the current coordinates to the coordinates of the next sample pixel to the converting to binary form of the sample pixel at the current coordinates are repeated when the sample pixel at the current coordinates is not the last sample pixel.

11. The method of claim 7, wherein the sampled pixel is represented by one of zero and one after being converted to binary form using a brightness value of the sampled pixel.

* * * * *